United States Patent
Farooq et al.

(10) Patent No.: US 9,267,105 B2
(45) Date of Patent: Feb. 23, 2016

(54) AMINOCLAY FOR HARVESTING ALGAE

(75) Inventors: Wasif Farooq, Daejeon (KR);
Young-Chul Lee, Daejeon (KR);
Ji-Won Yang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/371,718

(22) PCT Filed: Mar. 13, 2012

(86) PCT No.: PCT/KR2012/001801
§ 371 (c)(1),
(2), (4) Date: Jul. 10, 2014

(87) PCT Pub. No.: WO2013/105698
PCT Pub. Date: Jul. 18, 2013

(65) Prior Publication Data
US 2014/0335599 A1    Nov. 13, 2014

(30) Foreign Application Priority Data

Jan. 11, 2012  (KR) .................. 10-2012-0003511

(51) Int. Cl.
*C12N 1/12* (2006.01)
*C12Q 1/24* (2006.01)
*C12N 1/02* (2006.01)
*C07F 7/10* (2006.01)
*G01N 33/553* (2006.01)

(52) U.S. Cl.
CPC ... *C12N 1/12* (2013.01); *C07F 7/10* (2013.01); *C12N 1/02* (2013.01); *C12Q 1/24* (2013.01); *G01N 33/553* (2013.01)

(58) Field of Classification Search
None
See application file for complete search history.

(56) References Cited

U.S. PATENT DOCUMENTS

| | | | |
|---|---|---|---|
| 2011/0081706 A1 | 4/2011 | Schlesinger et al. | |
| 2013/0064776 A1* | 3/2013 | El Harrak et al. | 424/9.6 |

FOREIGN PATENT DOCUMENTS

| | | |
|---|---|---|
| KR | 10-0351619 B1 | 9/2002 |
| KR | 10-2004-0110040 A | 12/2004 |

OTHER PUBLICATIONS

Lee Y. et al. Removal of F-, NO3- and PO4-3 Ions from Aqueous Solution by Aminoclays. J of Industrial and Engineering Chemistry 18:871-875, 2012.*
English abstract of KR 10-0351619 B1, as captured from KIPO website on Nov. 11, 2014.
English abstract of KR 10-2004-0110040 A, as captured from KIPO website on Nov. 11, 2014.
Lee et al., "Harvesting of oleaginous Chlorella sp. by organoclays", Bioresource Technology, Jan. 29, 2013, vol. 132, pp. 440-445, Elsevier, Amsterdam, NL.
Lee et al., "Dual-end functionalized magnesium organo-(phyllo)silicates via co-condensation and its antimicrobial activity", Applied Clay Science, Sep. 4, 2013, vol. 83-84, pp. 474-485, Elsevier, Amsterdam, NL.
Lee et al., "Water-soluble organo-building blocks of aminoclay as a soil-flushing agent for heavy metal contaminated soil", Journal of Hazardous Materials, Sep. 6, 2011, vol. 196, pp. 101-108, Elsevier, Amsterdam, NL.
Han et al., "Magnesium and calcium organophyllosilicates: Synthesis and in vitro cytotoxicity study", ACS Applied Materials & Interfaces, May 25, 2011, vol. 3, No. 7, pp. 2564-2572, American Chemical Society, Washington, DC.
Sener et al., "The effect of silane modification on the adsorptive properties of natural pyrophyllite and synthetic titanium-based powders prepared by the sol-gel process", Turkish Journal of Chemistry, Oct. 2005, vol. 29, No. 5, pp. 487-495, Scientific and Technological Research Council of Turkey, Ankara, TR.
International Search Report for International Application No. PCT/KR2012/001801.

* cited by examiner

*Primary Examiner* — Ralph Gitomer
(74) *Attorney, Agent, or Firm* — Fanelli Haag PLLC

(57) ABSTRACT

The present invention relates to aminoclay, for harvesting algae, which is prepared by fixing aminosilane around cationic metal ions through a sol-gel reaction. Also, the present invention relates to a method for harvesting algae using the aminoclay according to any one selected from the above methods.

12 Claims, 7 Drawing Sheets

FIG. 1

Library of organoclay via sol-gel reaction

APTES    TMS    MTES    PTES    TE(M)OS $Mg^{2+}$
$Ca^{2+}$
$Al^{3+}$
$Fe^{3+}$
$Mn^{2+}$
$Zn^{2+}$
$Cu^{2+}$
$Ni^{2+}$
$Co^{2+}$

Note: APTES includse N1, N2, and N3 aminosilanes. And TTMS, MTES, PTES, and TE(M)OS indicate (3-mercaptopropyl)trimethoxysilane, methyltriethoxysilane, phenyltriethoxysilane, and tetraethoxy(methoxy)silane respectively.

AMINOCLAY FOR HARVESTING ALGAE

This application is a 35 USC 371 national stage application of co-pending International Patent Application No. PCT/KR2012/001801, filed on Mar. 13, 2012, which claims the benefit of Korean Patent Application No. 10-2012-0003511, filed on Jan. 11, 2012, each of which is hereby incorporated herein.

TECHNICAL FIELD

The present invention relates to a technique for harvesting green algae (often referred to as 'chlorophyceae'), and more particularly, to a proper concentration and time, and an amount of produced biomass, in harvesting (flocculation and settling) green algae using cationic organic nanoclays ('aminoclay'), wherein the technique is possibly applicable to all of green algae cultured in wastewater and tris-acetate-phosphate (TAP) medium. Further, the present invention relates to utilization of water-soluble cationic organic nanoclay, which is prepared by fixing aminosilanes around cationic metals ($Mg^{2+}$, $Ca^{2+}$, $Zn^{2+}$, $Mn^{2+}$, $Cu^{2+}$, $Co^{2+}$, $Ni^{2+}$, $Al^{3+}$, $Fe^{3+}$, etc.) (in order to form a clay structure) in the presence of an ethanol medium (any one solvent capable of dissolving a cationic metal precursor as well as aminosilane) through a sol-gel reaction, as specifically shown in FIG. 1 regarding green algae harvest.

BACKGROUND ART

Chlorophyceae (hereinafter, referred to as 'green algae') includeprocaryota (that is, blue-green algae) and eucaryota (that is, most of green algae), and have in general a photosynthetic pigment and are autotrophic like as plants. In other words, it is known that green algae generate oil and efficient ingredients by photosynthesis using light and carbon dioxide. Blue-green and green algae may occur a blooming to cause water contamination, however, are currently cultured in laboratories and fields for purposes of producing health substances such as EPA, DHA, etc., as well as useful carotinoid-based pigments present in cells of green algae. Furthermore, culturing green algae with a high lipid content may produce FAME (biodiesel) possibly used as a biofuel, thus coming into the spotlight.

In a process of manufacturing algal (green algal) biodiesel, in particular, in downstream processes (culture, harvest/drying, extraction, and conversion to biodiesel), one among significant parts to reduce costs is green algae harvest. In particular, great energy is intensively required to harvest small cells (1 to 10 μm) from an extremely diluted solution, which is a significant problem that has yet to be overcome. Accordingly, there is still no certain way for rapidly and effectively harvesting green algae.

At present, techniques reported in the art may include, for example, centrifugation, flocculation, filtration, floating, pH control (to pH 11), or electrolysis method. However, these are energy consuming techniques, and it is not easy to use equipments for increasing efficiency thereof. Even though electrolysis method has better advantages, compared to other methods, this is a technique based on leakage of $Al^{3+}$ ions due to use of an electrode and application thereof, hence being cumbersome in use. Accordingly, development of appropriate techniques is still needed.

For flocculation method, use of existing cationic polymer or bioflocculant (bio-flocculation agent) produced by microorganisms has been reported. However, forms of water-soluble molecular ion and polymer have decreased efficiency.

In order to effectively harvest the green algae, as a positive value of zeta-potential of a molecule is concerned, the bigger the better. Furthermore, if the flocculant has strong cationic properties at a pH level ranging from 7 to 10 similar to conditions for green algae culture, green algae may be effectively harvested through flocculation. The reason for this is because the surface of green algae exhibits anionic properties. Furthermore, when using a flocculant in a particle form rather than ionic status, it is possible to find an alternative way capable of more effectively applying the flocculant and recovering the same. If the flocculant can be mass-produced and does not have residual toxicity, medium nutrients may be used in re-culture of green algae, thus considerably reducing unit cost of a product.

Accordingly, in order to solve the above-described problems, there is a need for a novel inventive flocculant in a particle type to rapidly and effectively harvest (that is, flocculation/sedimentation) the green algae.

DISCLOSURE

Technical Problem

Therefore, an object of the present invention is to provide an appropriate concentration and time at which biomass may be obtained by rapidly and effectively harvesting blue-green algae and green algae cultured in wastewater and TAP medium after synthesizing a cationic water-soluble organic nanoclay (particles) (with zeta-potential of +20 mV or more).

With regard to green algae harvest, conventional techniques involve disadvantages such as use of an apparatus or, even if a flocculant is used, decreased efficiency of the flocculant, or the like. Due to these circumstances, a definite solution has yet to be proposed. With regard to green algae culture, after harvesting green algae from a nutrient medium, the medium residue needs to be reused without further sanitary treatment in view of economical advantage. This means that growth of the green algae should not be prohibited by the used green flocculant if it remains. Further, in order to reduce an overall cost of green algae bio-refinery, the reused medium should be easily applied even in the case of green algae cultured in wastewater. Moreover, the green algae should be easily recovered even though different ingredients are present in the wastewater. Alternatively, in order to minimize an amount of the flocculant residue, it may be ideal that the flocculant has a particle form and exhibits cationic properties.

Technical tasks to be achieved by the present invention are not particularly limited to the above description, instead, alternative tasks not mentioned herein will be obviously understood from the detailed description of the present application by those skilled in the art, to which the present invention pertains.

Technical Solution

[1] Technical Means of the Present Invention

According to an aspect of the present invention, there is provided aminoclay for harvesting microalgae, which is prepared by fixing aminosilane around cationic metal ions through a sol-gel reaction.

The metal ions may include, for example, any one selected from a group consisting of $Mg^{2+}$, $Ca^{2+}$, $Zn^{2+}$, $Mn^{2+}$, $Cu^{2+}$, $Co^{2+}$, $Ni^{2+}$, $Al^{3+}$, $Fe^{3+}$.

The aminosilane stated herein may include, for example, any one selected from a group consisting of (3-aminopropyl)

triethoxysilane, [3-(2-aminoethylamino)propyl]trimethoxysilane and 3-[2-(2-aminoethylamino)ethylamino]propyltrimethoxysilane.

Preferably, the aminosilane may be a hybrid formed by combining at least one selected from a group consisting of TTMS (3-mercaptopropyl)trimethoxysilane), MTES (methyltriethoxysilane), PTES (phenyltriethoxysilane) and TEOS (tetraethoxysilane).

With regard to a mixing ratio of the metal ions and aminosilane, a molar ratio of the metal ions may be higher than a molar ratio of silicon (Si). Preferably, a mixing ratio of the metal ions and aminosilane may be 1:0.75 in terms of molar ratio of metal to silicon (Si).

The fixing stated herein may be executed in an organic solvent or distilled water. Preferably, the organic solvent is a solvent capable of dissolving at least one selected from a group consisting of cationic metal ions and organosilane. More preferably, the organic solvent is any one selected from a group consisting of ethanol, methanol, dimethylformamide (DMF) and dimethyl sulfoxide (DMSO). The organic solvent may actually function for fixation to wood, membrane, glass and/or fabrics (such as cotton, wool, nylon, polyester, etc.).

The fixation may be executed at a temperature of 5 to 30° C. and 1 atm.

The algae stated herein may include, for example, green microalgae or blue-green algae. In particular, the green algae are green microalgae cultured in wastewater, further, may be cultured in tris-acetate-phosphate (TAP) and even in a raceway pound. Meanwhile, following Table 1 describes in details information on physical properties of wastewater used in *Chlorella Vulgaris* culture.

TABLE 1

| Untreated beer wastewater | | Anaerobic treated beer wastewater | |
|---|---|---|---|
| Parameter | Values (mg/L) | Parameter | Values (mg/L) |
| COD | 2250-2300 | COD | 150-170 |
| BOD | 1300-1500 | BOD | — |
| pH | 5.45 | pH | 7-7.5 |
| TN | 10-21 | TN | 50-75 |
| TP | 12-16 | TP | 20-25 |
| TSS | 250-300 | TSS | 120-130 |

Hereinafter, the present invention will be described in more detail. FIG. 7 is a schematic view illustrating synthesis of organic nanoclay according to the present invention. In view of time-variant aspects, the synthesis will be described in detail as follows: a metal hydrate type substance (1.68 g) is dissolved in 40 mL of a water-soluble solution and organic solvent (BTEX, DMF, pyridine, DMSO, hexane, methanol, etc., preferably, ethanol with reduced toxicity as a representative example). After completely mixing and dissolving, about 2.6 mL of silane precursor is added thereto (herein, a molar ratio of metal cations>a molar ratio of silicon). For aminoclay, further addition of a catalyst is not required. After at least 6 hours, it reaches an equilibrium state. When using a silane precursor in another column of a clay library, a basic catalyst, that is, NaOH should be introduced to progress a sol-gel reaction. Accordingly, in case of organic nanoclay except for the aminosilane column, synthesis may be easily performed even in a water-soluble solution. When aminosilane is synthesized in a water-soluble solution base, immediately after particles are formed, those are dissolved in water. Therefore, it involves a drawback such as difficulties in recovering particles. However, water-solubility may be easily controlled by mixing the above substance with any other organosilane. In mass-production of organic nanoclay, a product may be simply manufactured by increasing amounts of reaction media, that is, ethanol and metal cationic silane precursor in proportion to the product and conducting the reaction. Such obtained product may be used after drying it in an oven at 50° C. overnight and then pulverizing the dried product in a mortar as a grinder.

More particularly, the aminoclay may be characterized by expressing cationic properties even at pH 4 to 10, so as to improve flocculation to the surface of green algae having anionic properties.

[2] Technical Means of Embodiment of the Present Invention

According to another aspect of the present invention, there is provided a method for harvesting algae using any one aminoclay selected from the above-described methods. More particularly, the aminoclay may be treated at a concentration of 0.5 to 0.25 g/L to harvest the green algae.

Advantageous Effects

The cationic water-soluble organic nanoclay ('aminoclay') of the present invention may have following beneficial features and effects.

1. When remaining in the water-soluble solution, aminoclay exhibits very little toxicity. Further, the nutrient medium can be reused without any problem. Even being exposed to external environments, safety may be ensured.

2. Because of a simple manufacturing method, mass-production can be accomplished, and even with a small amount thereof, green algae may be efficiently harvested. The inventive aminoclay may be physically combined (admixed) with other cheap flocculants, and especially, more efficient as the higher a cell concentration is.

3. When culturing the green algae in wastewater, even if the wastewater is discharged after harvest and sewage disposal, the cationic organic nanoclay (aminoclay) may inhibit the growth of green algae to thus be appropriately utilized.

4. Since the organic nanoclay has a nano-particle form, it may be controllably combined with effective components in a green algal cell, and in order to reuse the nanoclay, some ideas for fixing the same to wood, membrane, glass, fabrics (cotton, wool, nylon, polyester, etc.) or the like may also be deduced.

5. Meanwhile, in order to effectively harvest the green algae, as a positive value of zeta-potential of a molecule is concerned, the bigger the better. Further, if the flocculant has strong cationic properties at a pH level ranging from 7 to 10 similar to conditions for green algae culture, green algae may be effectively harvested through flocculation as described above. According to the present invention, advantageous results have been obtained even in the range of pH 4 to 10. Consequently, it may be determined that the flocculant may enable noticeably effective flocculation with the surface of green algae exhibiting anionic properties (see FIG. 6B).

DESCRIPTION OF DRAWINGS

FIG. 1 illustrates a library of cationic organic nanoclays. The nanoclay synthesized based on aminosilane in first column, refers to as 'aminoclay';

BEST MODE

Figure 2:
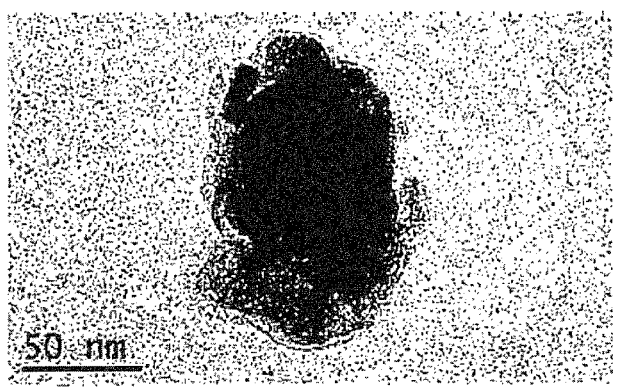
FIG. 2 illustrates dispersion of aminoclay around $Mg^{2+}$. Herein, it may be understood that —$NH_2$ site is subjected to protonation into —$NH_3^+$, hence exhibiting ammonia properties and forming organo-building blocks well dispersed due to repulsive force. In this figure, a transmission electron micrograph (TEM) of the dispersed organic nanoclay particles (upper part) as well as a fundamental structure thereof (lower part) are illustrated.
Figure 2:
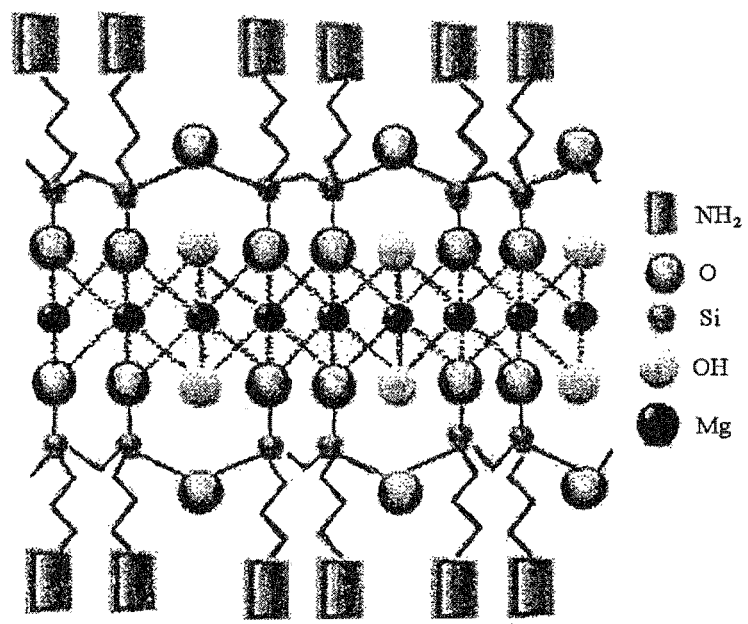
Figure 3A:
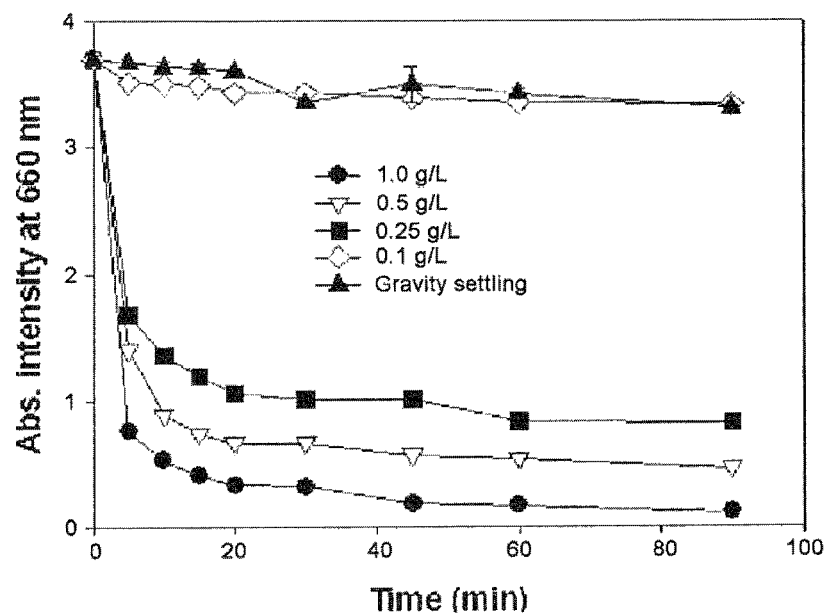
FIG. 3 illustrates a loading amount of organic nanoclay relative to a control, that is, a settlement rate by gravity with respect to *Chlorella Vulgaris* cultured in a TAP medium. For the organic nanoclay at a concentration of 1.0 to 0.25 g/L, most of green algae are settled (harvested) in a short time within 5 minutes, while a high harvest yield of at least 90% is monitored at concentration of 0.5 g/L. Accordingly, it is presumed that, if a small amount of organic nanoclay is loading, the harvest yield may be increased by extending the time. This may also be a measure to decrease an amount of clay to be used.
Figure 3B:
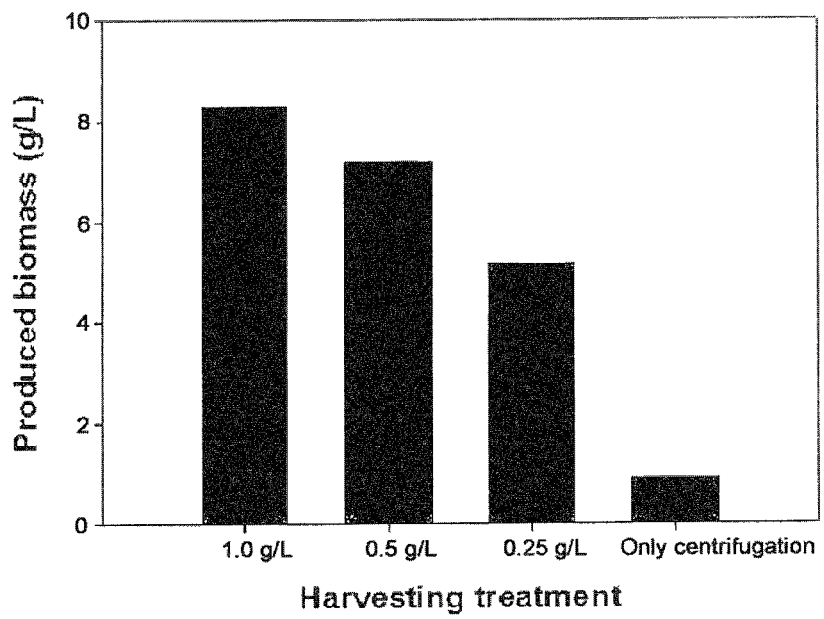
Figure 4:
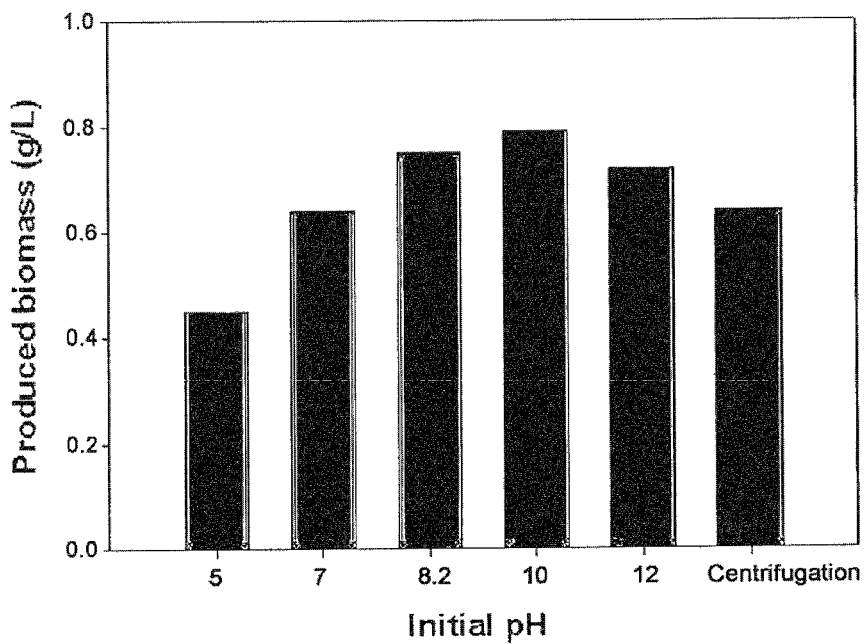
FIG. 4 illustrates harvest yields of green algae relative to pH values. Most of flocculants (ions or particles) have zeta-potential exhibiting anionic properties at pH 7.0 or higher, which means a charge on the surface thereof. Accordingly, the harvest yield at pH 7.0 to 10.0 is important since green algae are cultured in this range of pH values. From the figure, it can be seen that the organic nanoclay exhibits favorable cationic behavior under this pH condition (upper part), and as a result thereof, an optimal amount of biomass is produced (lower part).
Figure 5A:
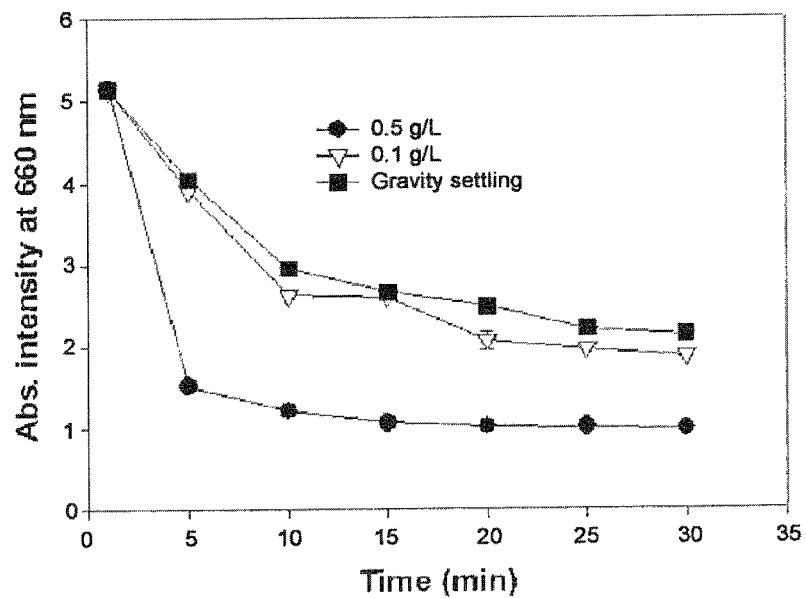
FIG. 5 illustrates settlement rates (upper part) of *Chlorella Vulgaris* at 0.5 and 0.1 g/L, respectively, which was cultured in wastewater. Like TAP medium, it can be seen that green algae are mostly harvested within 5 minutes. Interestingly, in case of wastewater, it is presumed that, since the green algae may be settled by nutrients formed due to microorganism colonies, harvest may be improved with decreased amount of organic nanoclay. Based on this ground, amounts of produced biomass are graphically illustrated and range from 1.0 to 1.2 g/L (lower part). Compared to a control, which is a product obtained by centrifugation at 5,000 rpm, the amount is slightly decreased but may be considered to be substantially similar to the control.
Figure 5B:
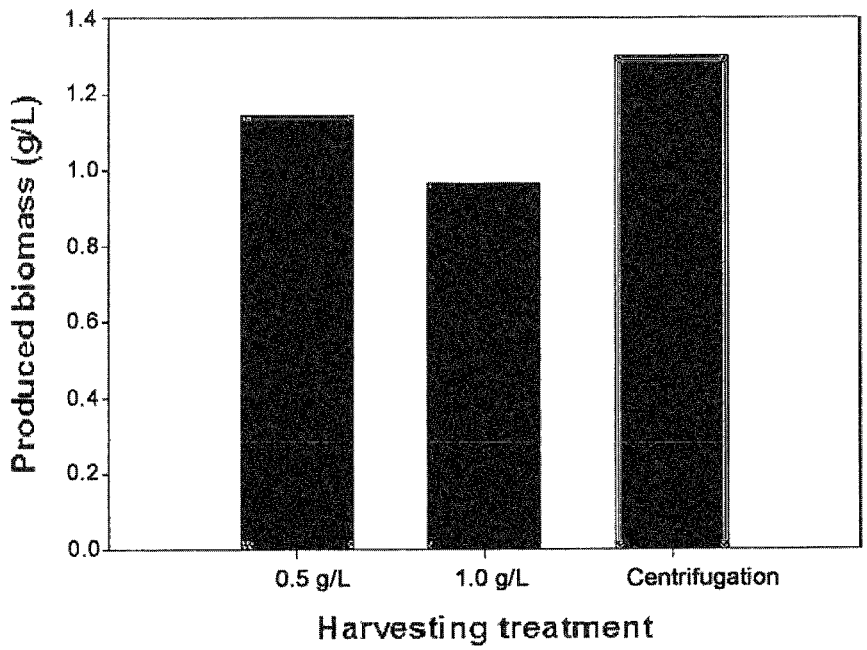
Figure 6A:
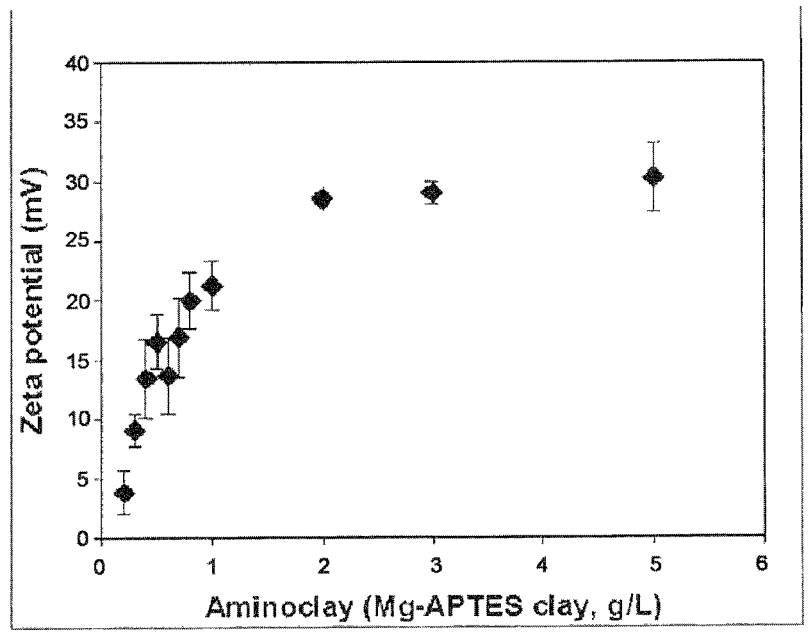
FIG. 6A illustrates zeta-potential values relative to loading (concentration) of aminoclay. More particularly, as the higher the concentration is, the more a positive degree of the charge value on the surface of aminoclay increases. In fact, it can be seen that such positive degree increases in geometric progression and then becomes saturated at 2.0 g/L or more. The reason of such a phenomenon exhibiting cations is because an amino site with a high density is to have protonic properties ('protonation'), that is, exhibits properties of quaternary ammonium, thus being transferred into cations. This is a reason why aminoclay has higher dispersibility and enables the aminoclay to be water-soluble.
Figure 6B:
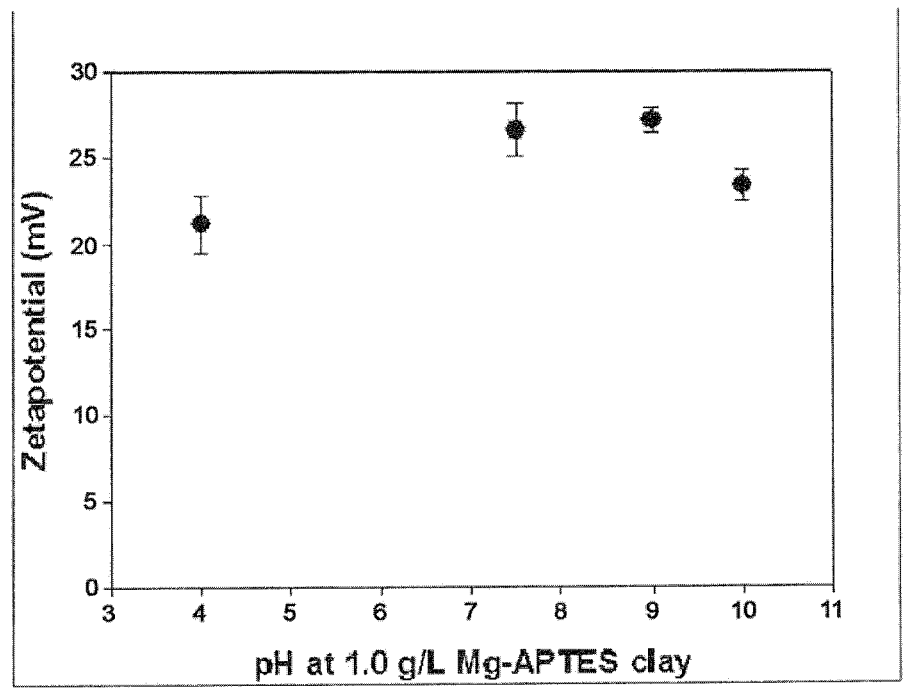
FIG. 6B illustrates zeta-potential values relative to pH values at a concentration of aminoclay of 1.0 g/L. Unlike most other nano-particles, the aminoclay has positive zeta-potential values in a wide range of pH values. As described above, the zeta-potential value is high and positive even at pH 4 to 10, demonstrating that the aminoclay may serve as an effective and excellent flocculant in harvesting green algae with a negative value of −20 mV or more.
Figure 7:
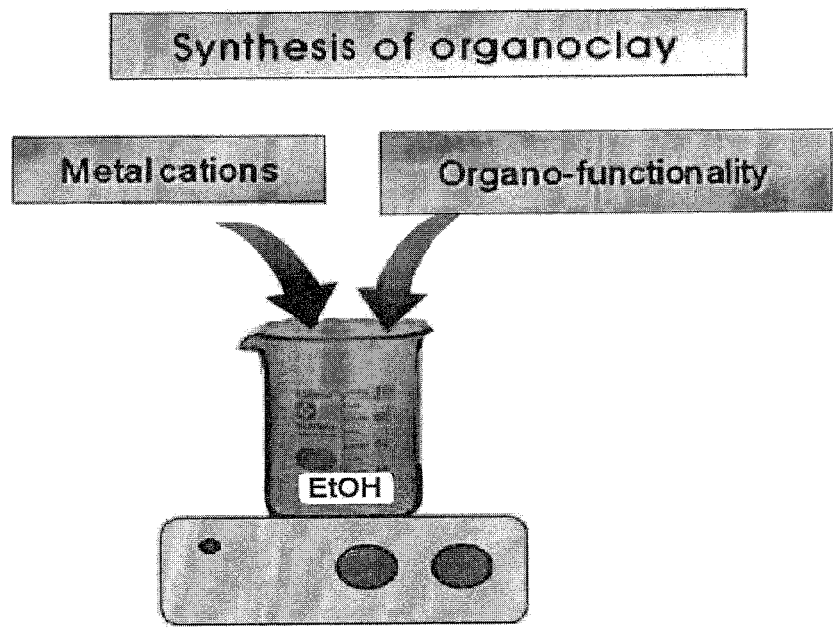
FIG. 7 is a schematic view illustrating synthesis of organic nanoclay of the present invention.

The present invention provides aminoclay for harvesting microalgae, including aminosilane fixed around cationic metal ions through a sol-gel reaction. Further, the present invention provides a method for harvesting algae using the aminoclay obtained by any one selected from the above described methods.

Since organic clay is biomimic, a water-soluble cationic clay rather than anionic clay is prepared in consideration of anionic properties on the surface of algae, and may be used to flocculate and harvest green algae through electrostatic attraction, as carried out by existing flocculants. Specifically, more improved effects may be presumed if it exhibits strong cationic properties in a range of pH 7.0 to 10 while having zeta-potential of +20 mV or more.

For biomimetic organic clay, it was found out from a water flea experiment that this substance is less toxic even at a high concentration, and according to zebra-fish experiments currently executed, the above clay demonstrated substantially no toxicity. In consideration of these results and on the basis of minimal inhibition concentration (MIC) deduced at 6 mg/mL (6,000 ppm) for most of microorganisms, it will be certainly understood that the cationic organic nanoclay (that is, aminoclay) at a lower concentration than the above may be used as a flocculant and efficiently applied to harvest of green algae.

Meanwhile, the aminoclay may have a concentration of 0.5 to 0.25 g/L. As shown in FIG. 1, such cationic water-soluble organic nanoclay (that is, aminoclay) may include an aminosilane-based substance containing cationic metal ions ($Mg^{2+}$, $Ca^{2+}$, $Zn^{2+}$, $Mn^{2+}$, $Cu^{2+}$, $Al^{3+}$, $Fe^{3+}$, etc.) in great quantities, in other words, at least one selected from aminosilane-based substances such as 3-aminopropyl)triethoxysilane (N1), [3-(2-aminoethylamino)propyl]trimethoxysilane (N2), 3-[2-(2-aminoethylamino)ethylamino]propyltrimethoxysilane (N3), or the like, which are fixed to metal ions through a sol-gel reaction, at the center thereof at ambient temperature/pressure without using any catalyst. The mixing stated herein may be executed at 5 to 30° C. under a condition of 1 atm, and the finally produced organic nanoclay may have a structure based on 2:1 trioctahedral, 2:1 and 1:1 dioctahedral phyllosilicate structures. A mixing ratio between aminosilane and metal cations as the cationic metal precursor stated herein may be about 1:0.75 in terms of molar ratio of metal to silicon (Si), and an amount of cationic metal may be defined by an excess amount. Alternatively, the present invention provides the cationic organic nanoclay (that is, aminoclay) prepared according to any one selected from the methods described above.

Hereinafter, the method for harvesting algae according to the present invention will be described in detail by the following experiments. Flocculation (harvesting) has been determined by measuring an optical density (OD) at 660 nm. A stock solution including aminoclay at 10.0 g/L (herein, aminoclay having an Mg backbone was used) was prepared and left overnight as it is, so as to completely release the same. The obtained aminoclay stock solution was applied to green algae (*Chlorella Vulgaris*) cultured in a TAB medium for 7 days (initial OD value is about 3.7 which is a value diluted by 10 times and measured) at an aminoclay concentration of 1.0, 0.5, 0.25 and 0.1 g/L, respectively. With maintaining abs. intensity to 1.0 or less by appropriate time interval (minutes), the mixture was diluted and OD value was measured, followed by multiplying the measured OD value with the number of dilute magnification. In this regard, for a control, gravity settlement was combined with the above procedures. Alternatively, an amount of produced biomass (g/L) was subjected to experiments along pH value. From the results of experiment, it was found that the amount of production was high at pH 7 to 10, that is, under typical culture conditions. As a control, the centrifugation method was considered. Green algae (*Chlorella Vulgaris*, initial OD value is about 5.14 which is a value measured in consideration of dilution) cultured in wastewater for 7 days was treated using a stock solution with an aminoclay concentration of 10.0 g/L, and the experiments were conducted while maintaining a final concentration to 0.5 and 0.1 g/L. As a control, the gravity settlement experiment was also combined with the above procedures. Flocculation (harvest) efficiency may be calculated from values before and after reaction, that is, [(O.D. at 660 nm before reaction minus (−) O.D. at 660 nm after reaction)/O.D. at 660 nm after reaction]×100. It is presumed that the method for harvesting the green algae using the aminoclay may be fast and convenient, and may simplify manufacturing processes. Further, a supernatant formed after flocculating reaction may be reused as a culture fluid without using an additional apparatus, thereby attaining advantages of reducing costs for water and nutrient salts required for culturing.

Figure 8:
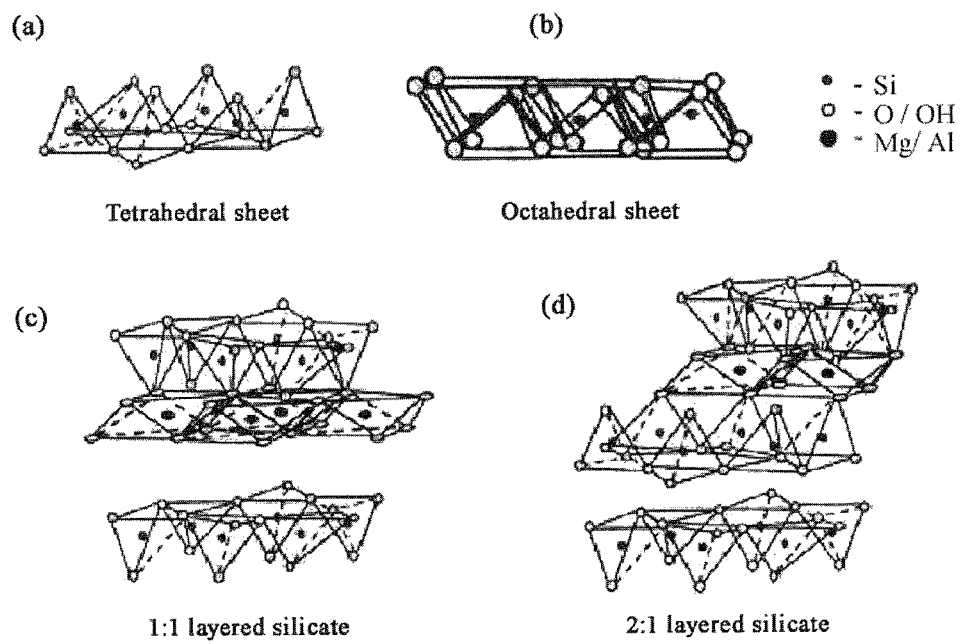
FIG. 8 illustrates (a) a tetrahedral sheet, (b) an octahedral sheet, (c) a 1:1 layered silicate structure, and (d) a 2:1 layered silicate structure.

Hereinafter, phyllosilicate will be described in more detail. FIG. 8 illustrates (a) a tetrahedral sheet, (b) an octahedral sheet, (c) a 1:1 layered silicate structure, and (d) a 2:1 layered silicate structure, respectively.

Phyllosilicate is a major constituent among mineral composition of clay. A basic building block consisting of phyllosilicate may be formed of a silica ($SiO_2$) face and an aluminum (Al) or magnesium (Mg) oxide-based octahedral face. A tetrahedral layer may include coordinate bonds between several silica tetrahedrons ($SiO_4$). Such a tetrahedron as described above may share four (4) oxygen atoms (O) in each of tetrahedron points not bonded in the same direction while forming a continuous face along three corners (FIG. 8(a)). These axes are linked from a tetrahedral face to an octahedral face, wherein oxygen atoms arranged in a direction perpendicular to the tetrahedral face are also shared by the octahedral face. On the octahedral face, Al or Mg atom is coordinated with six (6) oxygen atoms or OH groups, which are placed at the center or around Al or Mg atom. As shown in FIG. 8(b), the octahedral face derived from a peripheral side, at which OH groups or O atoms share the octahedral face, is present at each of octahedral corners. If the octahedral face includes 2+ ions such as $Mg^{2+}$, a charge balance may be attained when charges in a face are distributed over all sites. Such a face refers to as a trioctahedral face or brucite [Mg(OH)$_2$] face. If 3+ ions such as $Al^{3+}$ ions are included, only ⅔ of possible site is filled with the charges to maintain the balance in structure and a corresponding layer refers to as a gibbsite [$Al_2(OH)_6$] or dioctahedral face. An overall clay structure may be formed of a combination of another laminates of the tetrahedral and octahedral faces, wherein one face is linked to another face (see FIG. 8(c). A layered silicate may be classified by modes in which such basic building blocks are laminated with respect to the respective faces. Typical classification of phyllosilcate may mostly include 1:1, 2:1 and 2:1:1 layered silicate minerals. For 1:1 layered silicate (for example, kaolinite), each layer may include a tetrahedral face and an octahedral face. On the other hand, each layer in the 2:1 layered silicate is configured in such a manner that an octahedral face is sandwiched between two tetrahedral faces. Such a layer as described above should be fixed by weak van der Waals' force, so as to become neutral (for, example, talc) or, otherwise, may include cations between layers in order to attain a charge balance (for example, mica). The 2:1:1 type mineral may further have octahedral faces which are placed between respective tetrahedral, octahedral, and tetrahedral layers in a sandwich form, and each structure may be observed as a chlorite group mineral. A spacing formed between respective layers refers to as 011 or a basal spacing, and indicates a distance between two sequential layers.

As such, the present invention has been described with particular embodiments thereof. However, these embodiments are proposed only for illustrative purpose and the present invention is not particularly limited thereto. Various alterations or modifications of the above mentioned embodiments may be possible by those skilled in the art without departing from the scope of the present invention, and such alterations or modifications are duly included within the scope of the present invention. Substances of constituents described in the present specification may be easily selected and/or replaced from different materials known in the art by those skilled in the art. In addition, those skilled in the art may delete some among the constituents described in the present specification without deterioration in performance thereof or further include additional constituents in order to improve the performance. Furthermore, the order of methodical processes described in the present specification may be altered or changed according to processing environments or equipment. Accordingly, the scope of the present invention is not restricted by the embodiments described above but should be defined by appended claims and/or equivalents thereof.

INDUSTRIAL APPLICABILITY

As compared to existing flocculants, the present invention has advantages of rapidly and effectively harvesting green algae and ensuring safety, therefore, is considered to be very useful for industrial applications. Control and further research of cationic nano-particles may enable development of novel organic nanoclays capable of dissolving and/or penetrating a cellular membrane of the green algae. Furthermore, the present invention may establish a bridgehead for introduction of further techniques that attain both of green algae harvest and breakage of a cellular membrane of the green algae at once by any combination of some methods such as physical bead beating, sonication, microsaves, or the like, thereby being estimated to become an excellent technique throughout the world.

The invention claimed is:

1. Aminoclay for harvesting microalgae, which is prepared by fixing aminosilane centering around cationic metal ions through a sol-gel reaction.

2. The aminoclay according to claim 1, wherein the metal ions are selected from the group consisting of $Mg^{2+}$, $Ca^{2+}$, $Zn^{2+}$, $Mn^{2+}$, $Cu^{2+}$, $Co^{2+}$, $Ni^{2-}$, $Al^{3+}$, and $Fe^{3+}$.

3. The aminoclay according to claim 1, wherein the aminosilane is selected from the group consisting of (3-aminopropyl)triethoxysilane, [3-(2-aminoethylamino)propyl]trimethoxysilane and 3-[2-(2-aminoethylamino)ethylamino]propyltrimethoxysilane.

4. The aminoclay according to claim 1, wherein the aminosilane is a hybrid formed by mixing at least one selected from the group consisting of TTMS (3-mercaptopropyl)trimethoxysilane), MTES (methyltriethoxysilane), PTES (phenyltriethoxysilane) and TEOS (tetraethoxysilane).

5. The aminoclay according to claim 1, wherein a mixing ratio of metal ions to aminosilane is higher than one.

6. The aminoclay according to claim 5, wherein the mixing ratio of metal ions to aminosilane is 1:0.75.

7. The aminoclay according to claim 1, wherein the fixing is executed in an organic solvent or distilled water.

8. The aminoclay according to claim 7, wherein the organic solvent is a solvent for dissolving at least one selected from the group consisting of cationic metal ions, organosilane, and combinations thereof.

9. The aminoclay according to claim 8, wherein the organic solvent is selected from the group consisting of ethanol, methanol, dimethylformamide (DMF), dimethyl sulfoxide (DMSO) and combinations thereof.

10. The aminoclay according to claim 1, wherein the fixing is executed at 5 to 30° C. and 1 atm.

11. The aminoclay according to claim 1, wherein the microalgae is green algae or blue-green algae.

12. The aminoclay according to claim 1, wherein the aminoclay has cationic properties at pH 4 to 10 to increase flocculation to the surface of the microalgae exhibiting anionic properties.

* * * * *